United States Patent [19]

Kenna

[11] Patent Number: 5,047,056

[45] Date of Patent: Sep. 10, 1991

[54] CANINE HIP PROSTHESIS

[75] Inventor: Robert V. Kenna, Hobe Sound, Fla.

[73] Assignee: Pfizer, Inc., New York, N.Y.

[21] Appl. No.: 481,017

[22] Filed: Feb. 16, 1990

[51] Int. Cl.$^5$ .............................................. A61F 2/30
[52] U.S. Cl. ..................................................... 623/18
[58] Field of Search .............................. 623/16, 18, 23

[56] References Cited

U.S. PATENT DOCUMENTS

| | | | |
|---|---|---|---|
| 3,855,638 | 12/1974 | Pilliar | 623/18 |
| 4,550,448 | 11/1985 | Kenna | 623/18 |
| 4,589,883 | 5/1986 | Kenna | 623/18 |
| 4,666,450 | 5/1987 | Kenna | 623/18 |

OTHER PUBLICATIONS

The Richards Canine II Total Hip Replacement System Catalogue.
Mathyes Catalogue.
Benner,*DVM*, (Jul. 1987) pp. 30 and 52.

*Primary Examiner*—David J. Isabella
*Attorney, Agent, or Firm*—Pennie & Edmonds

[57] ABSTRACT

A canine hip prosthesis with a porous coating for bone ingrowth is disclosed. The femoral prosthesis generally comprises a stem for insertion into the intramedullary canal of a canine femur which stem is divided into a proximal portion and a longer distal portion. The stem exhibits a compound curvature along its length, including a slight posterior bow, which provides the prosthesis with a glove-like fit in the prepared intramedullary canal of the canine femur. Provided on the proximal portion of the stem is a porous coating which generally comprises two layers of ball-shaped metallic particles bonded together at their points of contact, e.g. by sintering, which define between themselves a plurality of connected interstitial pores. The size of the particles is from −30 to +35 U.S. Standard mesh size, and the pore size is between about 0.014 and 0.020 inches. The porous coating described provides superior resistance to failure at the coating-substrate and coating-bone interfaces, without weakening the prosthesis. The porous coating disclosed is also suitable for use in other canine bone prostheses.

27 Claims, 3 Drawing Sheets

CANINE HIP PROSTHESIS

BACKGROUND OF THE INVENTION

1. Technical Field of the Invention.

The present invention relates to a canine hip prosthesis, and more particularly to a femoral hip stem component and a porous coating for anchoring the stem in the intramedullary canal of the canine femur.

2. Description of Related Art.

Prior to the present invention a number of femoral inserts have been proposed for use in canine hip joint prostheses. Generally each of these included a polished spherical head or capitulum mounted on a stem, which stem is inserted into the intramedullary canal of the canine femur. Most often, the prior art inserts were cemented within the canal to hold them fast against the applied forces and loads. Some attempts have been made to anchor the insert without the use of cement by providing a mesh inset for the bone to grow into. These cementless inserts have not achieved optimum results.

It is well known in human medical practice to provide a metallic bone prosthesis with a porous metallic coating to enhance the fixation of the prosthesis to the patient's bone. Fixation of prostheses in humans by porous coatings, without the use of cement, has been found to eliminate several disadvantages associated with cemented fixation. In particular, these disadvantages include premature loosening of the prosthesis, tissue reaction with the cement and the need to remove large amounts of bone tissue to provide room for the cement. Tissue reaction and infection resulting from bone cement have been found to be more severe in dogs, making cementless fixation more desirable.

A variety of porous coatings have been proposed for human bone prostheses. For example, U.S. Pat. No. 3,855,638 discloses a porous coating for a surgical prosthetic device. However, this coating has been found unsuitable for use in human prosthetic devices because the small interstitial pore size and resulting porosity distribution tended to lead to failure of the bone at the coating-bone interface. For the same reason such a coating is unsuitable for canine applications. U.S. Pat. No. 4,550,448 discloses another porous coating for human bone protheses. This coating has been more successful due to its pore sizing and distribution, however, such a coating is unsuitable for use in canine bone prostheses. Use of the porous coating disclosed in the '448 patent in a canine femoral hip prosthesis would substantially degrade the strength of the prothesis due to the amount of stem material which would have to be removed to accommodate the coating thickness because the overall size of canine implant is significantly smaller than the human. This problem cannot be easily resolved by reducing the coating thickness because the thickness of the coating has been specifically designed for optimum bone ingrowth under human prosthetic conditions. To this point in time, a satisfactory porous coating for canine bone prostheses has not been developed.

Another problem in this field has been the overall shape of the insert. Prior art canine femoral hip prostheses have been provided with stems that exhibit a generally square cross-section and, except for an angled neck supporting the capitulum, exhibit substantially straight stems. Attempts have been made to computer model canine hip prostheses, however, these have proved less than satisfactory. One example of such a device has a wedge shaped stem which has exhibited a tendency to split the femur into which it is inserted.

The characteristics of the spacing or interface between the exterior surface of the prosthesis stem and the interior contour of the prepared cavity in the intramedullary canal play an important role in properly anchoring the insert to the femoral bone. A stem of sufficient length has long been recognized as desirable since it provides increased surface area for bone ingrowth within the canal and increased resistance to rotation. However, long stems require large intramedullary cavities, particularly at the calcar leading into the canal, since the overall surface thereof makes it difficult or impossible for the insert to pass into the canal without a significantly oversized entranceway. Such cavities result in large gaps or voids between the outside surface of the inserted stem and the inside surface of the cavity. Heretofore, a glove fit between a canine femoral stem and the intramedullary cavity together with superior anchoring of the stem and resistance to rotation have been considered difficult to achieve. Such a fit has been achieved in human femoral hip inserts (see, e.g. U.S. Pat. No. 4,589,883), but due to the different geometry of a human hip, this advance could not be used for canine applications.

SUMMARY OF THE INVENTION

Accordingly, an object of the present invention is a canine femoral hip prosthesis having a stem component that forms a glove fit when inserted into the intramedullary canal of a canine femur, the stem being properly anchored in place and having significant resistance to rotation.

Also, it is an object of the invention to provide a canine femoral hip prosthesis for fixation by bone tissue ingrowth, which fixation is highly resistant to failure at both the stem-coating and coating-bone interfaces, and within the coating, especially under cyclic loading conditions experienced by a canine hip prosthesis in use.

These and other objects of the invention are realized by providing a canine femoral hip prosthesis which may be inserted into the intramedullary cavity of a canine femur. The prosthesis comprises a stem which is divided generally into two parts, a proximal portion and a substantially longer distal portion. The stem, in cross-section, changes from nearly circular in the distal portion to non-circular, generally egg-shaped in the proximal portion. The egg-shape of the cross-section is due to the fact that the stem is substantially thicker on the medial face than on the lateral face. The overall shape of the stem follows a three-dimensional compound curvature defined by a transitional series of curves having different radii and orientations. The transitional series of curves matches the interior contour of the canine femur and thereby provides a glove-like fit between the stem and intramedullary cavity and positive resistance to rotation of the stem within the cavity.

The prosthesis is further provided with a trunnion neck portion, extending from the proximal portion of the stem, on which a capitulum is secured. The capitulum cooperates with either the natural acetabulum or an acetabular prosthesis. In a preferred embodiment the neck is anteverted at about 15° and inclined toward the medial face at about 45°.

In order to anchor the prosthesis within the canine femur, without the use of bone cement, the prosthesis is provided with a porous coating on the exterior surface of the proximal portion. The porous coating comprises two layers of metallic spherical particles bonded to a substrate material, which is the proximal portion of the stem. The layers of particles are further bonded together at their points of contact to form a three-dimensional network of connected interstitial pores.

In a preferred embodiment the particles are from −30 to +35 U.S. Standard Mesh size. The particles in the layers are distributed upon the exterior surface of the proximal portion at substantially uniform surface densities with the distribution such that at any level of the porous coating the pores occupy approximately 22% to 55% of the surface area at that level.

In the porous coating according to the invention the porosity and average pore size of the coating in the second or top layer are substantially greater than in the first or inside layer.

BRIEF DESCRIPTION OF THE DRAWING

Novel features and advantages of the present invention in addition to those mentioned above will become apparent to those skilled in the art from a reading of the following detailed description in conjunction with the accompanying drawing wherein.

DETAILED DESCRIPTION OF THE INVENTION

Figure 3:
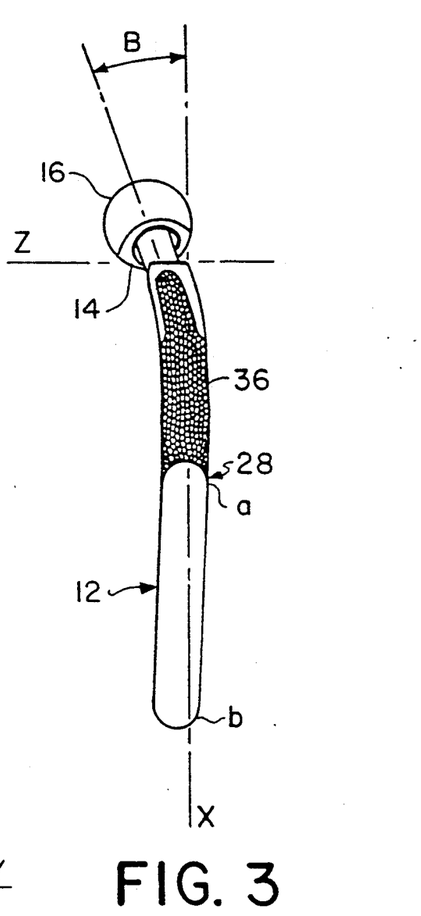
FIG. 3 is a right side elevational or lateral view of the prosthesis shown in FIG. 1.
Figure 4:
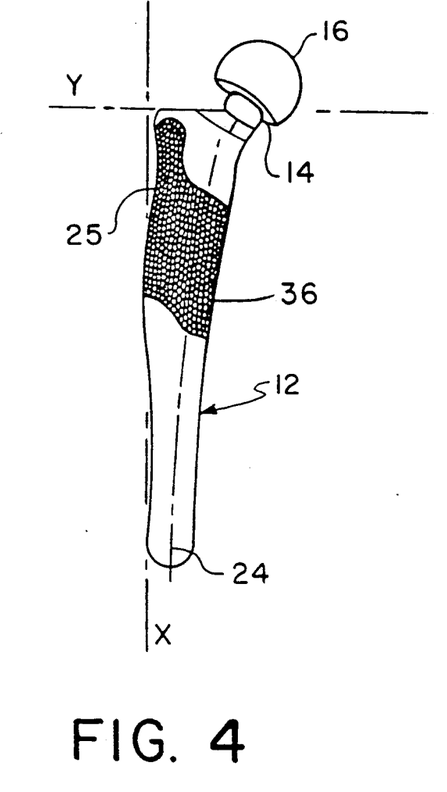
FIG. 4 is a rear elevational or posterior view of the prosthesis shown in FIG. 1.
Figure 5:
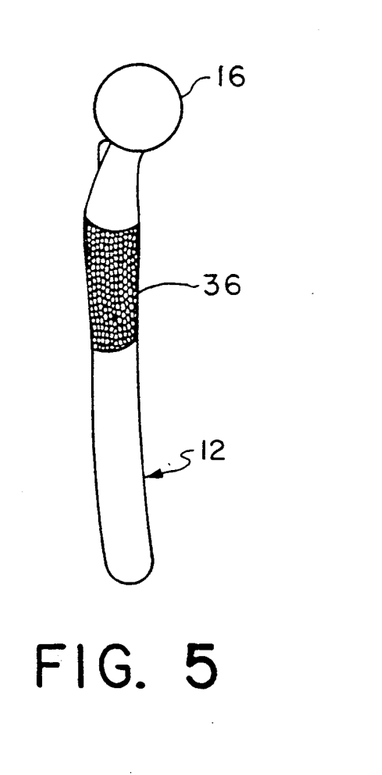
FIG. 5 is a left side elevational or medial view of the prosthesis shown in FIG. 1.

Referring to the drawing, a canine femoral hip prosthesis 10 includes a stem component 12 having a neck 14 to which a capitulum 16 is secured. FIGS. 1–5 illustrate a left hip prosthesis having an anterior face (FIG. 1), a posterior face (FIG. 4), a lateral face (FIG. 3), and a medial face (FIG. 5). In order to assist in the understanding of the present invention, the prosthesis 10 is shown with an associated axes system wherein the positive X axis extends from the bottom of the prosthesis, the positive Y axis extends from the lateral face and the positive Z axis extends from the anterior face. As explained more fully below, the stem 12 tightly fits within a prepared intramedullary cavity 18 of a left canine femur 20. The fit of the stem within the cavity is glove-like without any void or gap therebetween.

The stem 12 is generally divided into a proximal portion 22 and a substantially longer distal portion 26. The proximal portion 22 is generally covered over its exterior surface with a porous coating 36 that provides a means for bone ingrowth to anchor the prosthesis 10. The length of the distal portion 26 is preferably about 1½ to 2 times the length of the proximal portion 22 as measured along the lateral face (FIG. 3). As shown best in FIGS. 3 and 5, stem 12 has a very slight posterior bow 28 along its length. The bow 28 is manifested as a relatively greater distance between the X axis and the posterior face at point (a) as compared to between the X axis and the posterior face at point (b).

The posterior bow 28 forms part of a complex or compound three-dimensional curvature of the stem 12 created by a transitional series of curves having different radii and orientations. The general orientation of the compound curvature is along double-dashed line 24. This curvature includes very slight changes in direction of the stem 12 and may be defined as a curvature that matches the internal contour of the intramedullary cavity 18 of the femur 20. The stem 12 is shaped to match the cavity 18 by computer analysis of discrete cross-sections of canine femurs to ensure a glove-like fit for the stem 12 within the cavity 18. The posterior bow 28 is one of the gross features of the compound curvature. It is a curve having a large radius of about 6 inches. Also, in FIG. 1, it can be seen that the stem has a general curvature along double-dash line 24, which curvature has a radius of approximately 9 inches. The shape of the stem 12 aids in securing the stem 12 within the femur 20 while preventing rotation relative to the femur 20.

In addition to the general posterior bow 28, the curvature of the stem 12 toward the anterior face increases in the proximal portion 22. This can be most clearly seen in FIG. 3 where the upper end of the proximal portion 22 curves more sharply toward the anterior face than in the lower part of the proximal portion 22. Also in the proximal portion 22, the stem 12 has a slight inward or concave curvature 25 of the lateral face, which can be seen most clearly in FIGS. 1 and 4.

Figure 7:
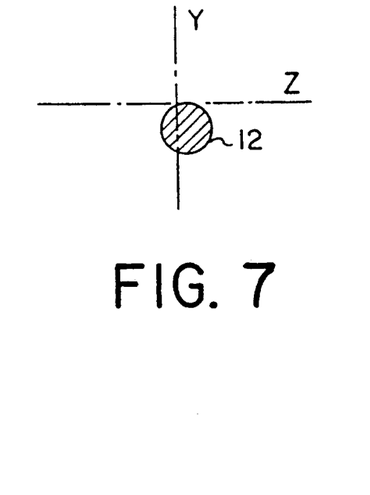
FIG. 7 is a sectional view taken along line 7—7 of FIG. 1.
Figure 8:
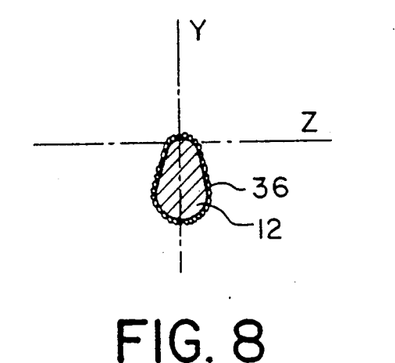
FIG. 8 is a sectional view taken along line 8—8 of FIG. 1.
Figure 9:
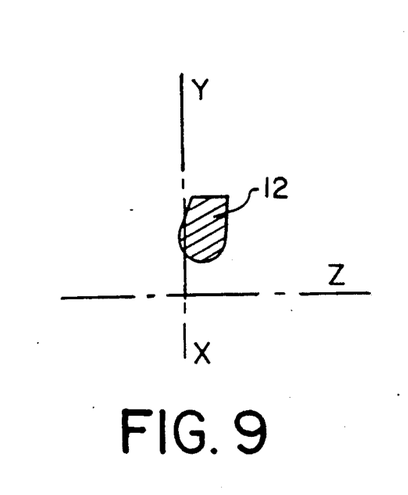
FIG. 9 is a sectional view taken along line 9—9 of FIG. 1.

Another important feature of the canine femoral hip prosthesis according to the invention may be seen in the variation of the cross-section of the stem 12 throughout its length. This feature is that the heaviest or thickest part of the stem 12 occurs on the medial face. This is directly opposite from the shape of hip implants designed for use in human femurs, such as the prosthesis disclosed in U.S. Pat. No. 4,589,883, discussed above with the related art. As can be seen in FIG. 7, in the present invention, the cross-section of the stem 12 at the lower end of the distal portion 26 is circular or almost circular. This cross-section transitions into a generally egg-shaped cross-section in the proximal portion 22, as is shown in FIG. 8. The egg-shape of the cross-section begins to develop at about the middle of the distal portion 26 and is fully developed at the lower end of the proximal portion 22. This egg-shape (FIG. 8) is substantially constant throughout the proximal portion 22. Ultimately, at the upper end of the proximal portion 22 (FIG. 9), the egg-shape of the cross-section becomes squared off on one side in order to accommodate the neck 14.

Figure 1:
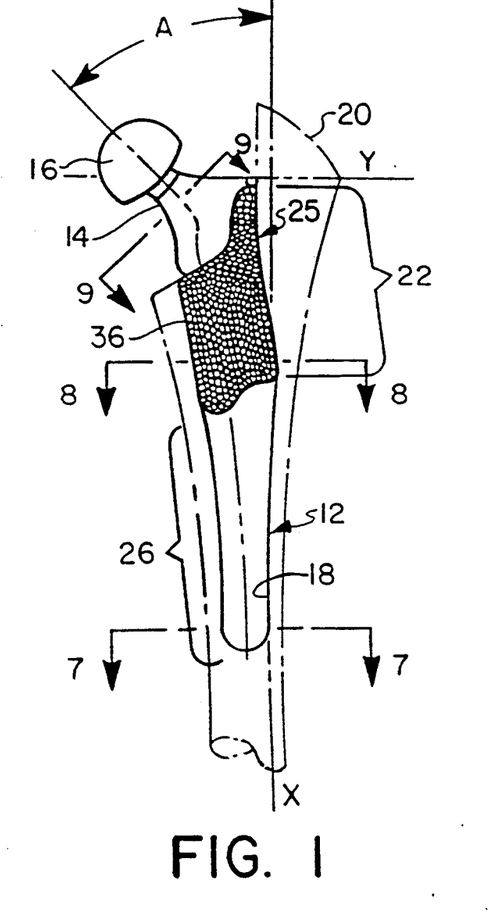
FIG. 1 is a front elevational or anterior view of a left canine femoral hip prosthesis according to the present invention.
Figure 10:
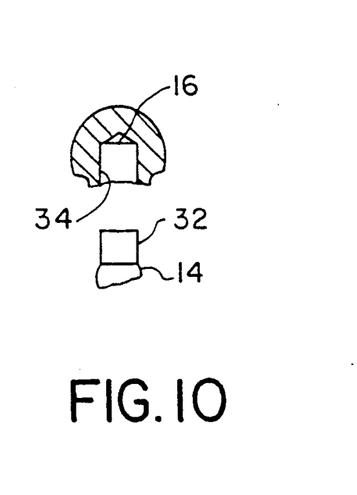
FIG. 10 is a partial exploded view of the prosthesis shown in FIG. 1, with the capitulum shown in cross-section.
Figure 11:
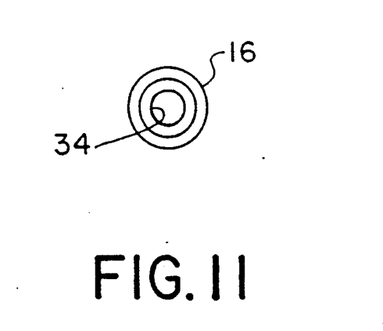
FIG. 11 is a bottom plan view of the capitulum.

Neck 14 of the prosthesis 10 may be generally described as a trunnion neck. As best shown in FIGS. 1 and 4, it is disposed at an angle A of about 45° to the general orientation of stem 12. The neck 14 has a tapered free end portion 32 (FIG. 10) which cooperates with a tapered internal socket 34 in the capitulum 16. In a preferred embodiment, the tapering characteristics of end portion 32 and socket 34 are such that a Morse fit results when the capitulum 16 is secured on to the neck 14.

As is well known, the capitulum 16 is in the form of a polished spherical element which articulates with the natural acetabulum, or with an acetabular prosthesis if the natural acetabulum has been replaced. A suitable canine acetabular prosthesis may be designed to function similarly to the human acetabular cup assembly prosthesis disclosed in U.S. Pat. No. 4,466,450 to Kenna, incorporated herein by reference. In a preferred embodiment for canine prostheses such an acetabular cup is secured against rotation by a single peripheral peg and provided on its exterior surface with a porous coating, similar to that described below, in order to anchor the cup without the use of bone cement or screws.

Figure 2:
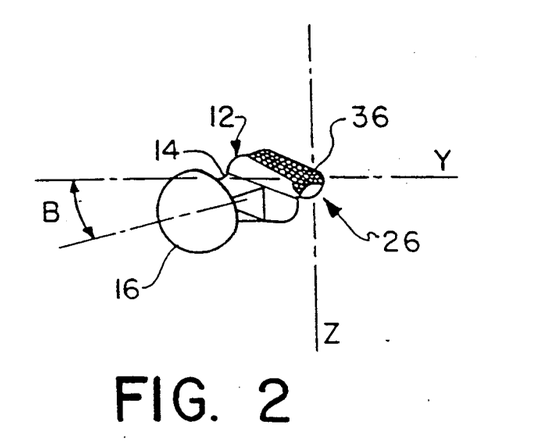
FIG. 2 is a top plan view of the prosthesis shown in FIG. 1.

Neck 14 and its associated capitulum 16 are anteverted at an angle B of about 15°. As shown in FIGS. 2 and 3, this anteversion results in the capitulum 16 being angled slightly toward the anterior face by about 15°. Such anteversion places the capitulum 16 in the best possible position for articulation with the natural acetabulum or acetabular prosthesis. Unlike human prosthesis, such as in the '883 patent referred to above, where the anteversion of the neck in preferred embodiments may vary through a small range, the anteversion of the neck 14 in a preferred embodiment of the canine femoral hip prosthesis 10 according to the present invention is more particularly 15°. This is not to say, as should be readily apparent to one skilled in the art, that slight variation is not possible in specific alternative embodiments.

The femoral hip prosthesis 10 is implanted within the femur 20 following femoral neck osteotomy and proper formation of the intramedullary cavity 18 into which stem 12 of the prosthesis 10 is to be inserted. In forming the intramedullary cavity 18 a portion of the cancellous tissue near the end of the femur 20 initially is cut away with an appropriate cutting tool (not shown). Following such removal, a rasp (not shown) having the same general shape as stem 12 is driven into the intramedullary canal of the femur 20. The rasp is then withdrawn from the femur 20 and the stem 12 introduced into the thus formed intramedullary cavity 18. Stem 12 passes into intramedullary cavity 18 without violating or interrupting the newly formed contour shaped by the rasp. The posterior bow 28 together with the further curvature in the proximal portion and the overall three-dimensional compound curvature of the stem enables such insertion of the stem into the intramedullary cavity 18 and results in a glove-like fit substantially free of gaps or voids between the exterior surface of the stem 12 and the interior contour of the prepared cavity 18.

With prosthesis 10 in two pieces, comprising stem 12 and capitulum 16 (FIG. 10), multiple neck lengths can be obtained with a single stem 12 by using capitulums having different internal sockets 34. For example, when a long neck length is desired, the internal socket 34 in the capitulum 16 may be short, and with a long internal socket 34 a shorter neck length is achieved with the same stem 12. Both stem 12 and capitulum 16 may be fabricated of, for example, cobalt/chromium/molybdenum or titanium by techniques known in the art.

Porous coating 36 on proximal portion 22 stimulates bone ingrowth and thus provides cementless anchoring means for the prosthesis 10 within femur 20. Shown in detail in FIG. 6, the porous coating 36 comprises a multiplicity of generally spherical particles 38 bonded together and to the proximal portion 22 of the stem 12 at their points of contact 30 by a sintering process. The particles 38 define between themselves a three-dimensional network of interconnected interstitial pores 40. The coating actually consists of first and second monolayers 42 and 44 of particles 38. The particles in first layer 42 are bonded to both the stem 12 and second layer 44. Suitable materials and means for manufacturing such a porous coating are disclosed in U.S. Pat. No. 4,550,448 to Kenna, incorporated herein by reference.

Figure 6:
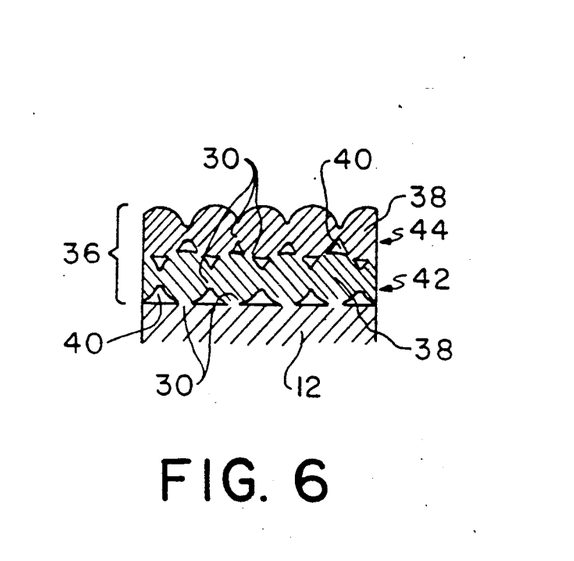
FIG. 6 is an enlarged side view in section of a portion of the prosthesis of FIG. 1 that includes the porous coating according to the present invention.

In the porous coating 36 of the present invention the size of the particles selected is from −30 to +35 U.S. Standard mesh size. The average size of such particles is about 0.022 inches. Using this size particle, the pore size of the coating 36 in the present invention is maintained in the range of between about 0.014 inches to about 0.020 inches (350-500 microns) in order to ensure proper bone ingrowth. As used herein, pore size refers to the largest dimension across a pore in any direction. This particle size is necessary to provide a porous coating which extends the required amount, about 0.006 to 0.007 inches, beyond the adjacent smooth exterior surfaces of the stem 12. The particle size is restricted because the undercut in the proximal portion 22, which accommodates the monolayers 42 and 44 of particles 38 making up the porous coating 36, should preferably not exceed 0.040 inches in order ensure adequate strength of the stem 12 in the undercut area. If excessive material is cut away the strength of the stem 12 may be severely degraded. The desired overall height of the porous coating is between about 0.040 inches and about 0.047 inches.

In order to ensure sufficient strength for the porous coating itself, the minimum bond diameter should be no less than 30% of the particle size. The bond diameter is the size of the bonds formed between the individual particles 38 at their points of contact 30. In a preferred embodiment of the present invention the average bond diameter is about 40% of the particle size. This provides an average bond diameter of about 0.0088 inches. Bond diameters substantially less than this significantly weaken the porous coating, while bond diameters substantially greater reduce the overall porosity of the coating significantly.

The porosity of a structure such as the porous coating 36 of the present invention will vary depending on the distance from the substrate material, in this case the exterior surface of the proximal portion 22 of the stem 12. The porosity at a given layer in the coating 36 may be defined as a percentage of total area at that layer which is occupied by empty space, e.g. by pores. In the present invention the porosity thus defined falls in the range of between about 22% to about 55% depending on the distance from the substrate at which the porosity is measured. The percent porosity varies substantially over the thickness because, for example, at the approximate center of layer 42, where the greatest amount of bonding between the particles in that layer occurs, there will be the minimum amount of unoccupied space to create porosity. The opposite is true at the approximate meeting line of layers 42 and 44 because this is where a maximum amount of unoccupied space will occur.

In a particularly preferred embodiment, the canine femoral hip prosthesis according to the present invention comprises a stem, capitulum and acetabular cup generally as described above, and further includes all of the following specific features, discussed individually above. In this embodiment, the stem 12 has a slight posterior bow over its length, and in the proximal portion 22 is substantially thicker on the medial face than on the lateral face. Extending from the proximal portion 22 is a trunnion neck 14 on which the capitulum 16 is secured. The capitulum 16 cooperates with an acetabular cup that is secured against rotation by a single peripheral peg. The stem, over the surface of proximal portion 22, and the acetabular cup are provided with a porous coating 36 comprising a multiplicity of metalic spherical particles 38 from −30 to +35 U.S. standard mesh size and defining there between a plurality of interstitial pores 40 being from about 0.014 to about 0.020 inches in their largest dimension.

The description of preferred embodiments contained herein is intended to in no way limit the scope of the invention. As will be apparent to a person skilled in the art, various modifications and adaptions of the structure above described will become readily apparent without departure from the spirit and scope of the invention, the scope of which is defined in the appended claims.

What is claimed is:

1. A canine femoral hip prosthesis for insertion into the intramedullary cavity of a canine femur, comprising a stem with an anterior face, a posterior face, a lateral face and a medial face, and having a proximal portion and a substantially longer distal portion, the stem transitioning from a nearly circular cross-section in the distal portion to a non-circular cross-section in the proximal portion with the stem in the proximal portion being substantially thicker on the medial face than on the lateral face, said stem having a slight posterior bow and further exhibiting a three-dimensional compound curvature defined by a transitional series of curves having different radii and orientations, said transitional series of curves matching the interior contour of the canine femur and thereby providing a glove-like fit between the stem and intramedullary cavity and positive resistance to rotation of the stem within the cavity.

2. A canine femoral hip prosthesis as in claim 1 wherein:
   the stem in the proximal portion has a generally egg-shaped cross-section;
   the proximal portion has a slight concave curvature along the lateral face; and
   the curvature of stem in the proximal portion increases toward the anterior face.

3. A canine femoral hip prosthesis as in claim 2 wherein the length of the distal portion is approximately 1½ to 2 times the length of the proximal portion as measured along the lateral face.

4. A canine femoral hip prosthesis as in claim 3 further comprising a trunnion neck extending from the proximal portion, the neck having an axis at an angle of about 45° to the general orientation of the stem.

5. A canine femoral hip prosthesis as in claim 4 wherein the neck is anteverted at an angle of about 15°.

6. A canine femoral hip prosthesis as in claim 5 further comprising a capitulum secured to the neck.

7. A canine femoral hip prosthesis as in claim 6 wherein the capitulum and the neck are secured together by a Morse fit.

8. A canine femoral hip prosthesis as in claim 1 wherein the exterior surface of the proximal portion includes a porous coating.

9. A canine femoral hip prosthesis for insertion into the intramedullary cavity of a canine femur, comprising a stem with an anterior face, a posterior face, a lateral face and a medial face, and having a proximal portion and a substantially longer distal portion, the stem transitioning from a nearly circular cross-section in the distal portion to a non-circular cross-section in the proximal portion with the stem in the proximal portion being substantially thicker on the medial face than on the lateral face, said stem having a slight posterior bow and further exhibiting a three-dimensional compound curvature defined by a transitional series of curves having different radii and orientations, said transitional series of curves matching the interior contour of the canine femur and thereby providing a glove-like fit between the stem and intramedullary cavity and positive resistance to rotation of the stem within the cavity, and wherein the proximal portion includes a porous coating consisting essentially of first and second layers of metallic spherical particles having average diameters of about 0.022 inches bonded together at their points of contact to define therebetween a plurality of connected interstitial pores.

10. A canine femoral hip prosthesis as in claim 9, wherein:
   the porous coating comprises a multiplicity of spherical metallic particles with said plurality of connected interstitial pores extending through said porous coating to the exterior surface of the proximal portion of the prosthesis;
   the particles in said first layer are bonded to said exterior surface and said first layer is bonded to said second layer with a minimum bond diameter between said particles of 30% of the particle diameter; and
   the particles in said first and second layers are distributed upon said exterior surface and upon said first layer, respectively, at substantially uniform surface densities with the particles in said first and second layers being from −30 to +35 U.S. Standard mesh size and the largest dimension of said interstitial pores being within the range of about 0.014 inches to about 0.020 inches, and the distribution of said particles in each of said layers is such that, at any level of the porous coating the pores occupy between about 22% to about 55% of the area of that level.

11. A canine femoral hip prosthesis as in claim 10 wherein the porosity and average pore size of the porous coating in said second layer are substantially greater than in said first layer.

12. A canine femoral hip prosthesis as in claim 10 wherein the thickness of the porous coating is from about 0.040 inches to about 0.047 inches.

13. A canine femoral hip prosthesis as in claim 10 wherein the average bond diameter is 0.0088 inches.

14. A canine femoral hip prosthesis comprising a stem having a proximal portion and a substantially longer distal portion, and a porous coating on the exterior surface of the proximal portion, wherein said porous coating comprises a multiplicity of spherical metallic particles bonded together at their points of contact, and with said particles defining between themselves a plurality of connected interstitial pores extending through said porous coating to the exterior surface of the proximal portion of the prosthesis, and wherein said porous coating consists essentially of first and second layers of said particles, with the particles in said first layer being bonded to said exterior surface and said first layer being bonded to said second layer with a minimum bond diameter between said particles of 30% of the particle diameter, the particles in said first layer and said second layer being distributed upon said exterior surface and said first layer, respectively, at substantially uniform surface densities and the particles in said first layer and said second layer being from −30 to +35 U.S. Standard mesh size with the largest dimension of said pores being between about 0.014 inches and about 0.020 inches, and the distribution of said particles in each of said layers is such that, at any level of the porous coating the pores occupy between 22% to 55% of the area or that level.

15. The porous coating as in claim 14 wherein the porosity and average pore size in said second layer are substantially greater than in said first layer.

16. The porous coating as in claim 14 wherein the thickness of said porous coating is from about 0.040 inches to about 0.047 inches.

17. The porous coating as in claim 14 wherein the average bond diameter is about 0.0088 inches.

18. A canine femoral hip prosthesis for insertion into the intramedullary cavity of a canine femur, comprising:
   a stem with an anterior face, a posterior face, a lateral face and a medial face, and having a proximal portion with an exterior surface that includes a porous coating bonded to said exterior surface and comprising first and second layers of metallic spherical particles having average diameters of about 0.022 inches bonded together at their points of contact to define therebetween a plurality of connected interstitial pores, and said stem having a distal portion approximately 1½ to 2 times the length of the proximal portion as measured along the lateral face, said stem transitioning from a nearly circular cross-section in the distal portion to a non-circular cross-section in the proximal portion with said stem in the proximal portion being substantially thicker on the medial face than on the lateral face, said stem having a slight posterior bow with the curvature of the stem at the upper end of the proximal portion increasing toward the anterior face, said stem further exhibiting in the proximal portion a slight concave curvature along the lateral face;
   an anteverted neck extending from the proximal portion of the stem at an angle to the general orientation of the stem in the direction of the medial face; and
   a capitulum secured to the neck.

19. A canine femoral hip prosthesis as in claim 18 wherein the stem further exhibits a three-dimensional compound curvature defined by a transitional series of curves having different radii and orientations, said transitional series of curves substantially matching the interior contour of the canine femur and thereby providing a glove-like fit between the stem and intramedullary cavity and positive resistance to rotation of the stem within the cavity.

20. A canine femoral hip prosthesis as in claim 18 wherein:
   the neck is anteverted at an angle of about 15°; and
   the neck extends toward the medial face at an angle of about 45°.

21. A canine femoral hip prosthesis as in claim 18 wherein the thickness of the porous coating is from about 0.040 inches to about 0.047 inches.

22. A canine femoral hip prosthesis as in claim 18 wherein the bonded metallic particles have a minimum bond diameter of 30% of the particle diameter.

23. A canine hip prosthesis comprising in combination:
   a canine acetabular cup prosthesis having a peripheral peg to secure said cup against rotation and a porous coating to anchor said cup in a canine acetabulum; and
   a canine femoral hip prosthesis for insertion into a canine intramedullary canal according to claim 1, wherein said femoral prosthesis includes a capitulum at the proximal end and said capitulum is partially surrounded by and rotatably secured within the acetabular cup.

24. A canine hip prosthesis comprising in combination:
   a canine acetabular cup prosthesis having a peripheral peg to secure said cup against rotation and a porous coating to anchor said cup in a canine acetabulum; and
   a canine femoral hip prosthesis for insertion into a canine intramedullary canal according to claim 8, wherein the capitulum is partially surrounded by and rotatably secured within the acetabular cup.

25. A canine hip prosthesis comprising in combination:
   a canine acetabular cup prosthesis having a peripheral peg to secure said cup against rotation and a porous coating to anchor said cup in a canine acetabulum; and
   a canine femoral hip prosthesis for insertion into a canine intramedullary canal according to claim 18, wherein the capitulum is partially surrounded by and rotatably secured within the acetabular cup.

26. A canine bone prosthesis comprising a substrate of metallic material and a porous coating of said metallic material bonded to and extending over at least a portion of the exterior surface of the substrate, wherein:
   the porous coating comprises a multiplicity of spherical metallic particles bonded together at their points of contact to define therebetween a plurality of connected interstitial pores and said porous coating consists essentially of first and second layers of said metallic spherical particles with said plurality of connected interstitial pores extending through said porous coating to the exterior surface of the substrate;
   the particles in said first layer are bonded to said exterior surface and said first layer is bonded to said second layer with a minimum bond diameter between said particles of 30% of the particle diameter; and
   the particles in said first and second layers are distributed upon said exterior surface and said first layer, respectively, at substantially uniform surface densities with the particles in said first and second layers being from −30 to +35 U.S. Standard mesh size and the largest dimension of said interstitial pores being from about 0.014 inches to about 0.020 inches, and the distribution of said particles in each of said layers is such that, at any level or the porous coating said interstitial pores occupy between about 22% to about 55% of the area of that level.

27. A canine femoral hip prosthesis for insertion into the intramedullary cavity of a canine femur, comprising a stem with an anterior face, a posterior face, a lateral face and a medial face, and having a proximal portion and a substantially longer distal portion, the stem transitioning from a nearly circular cross-section in the distal portion to a non-circular cross-section in the proximal portion with the stem in the proximal portion being substantially thicker on the medial face than on the lateral face, said stem having a slight posterior bow with the curvature of the stem at the upper end of the proximal portion increasing toward the anterior face, said stem further exhibiting in the proximal portion a slight concave curvature along the lateral face and wherein the exterior surface of the proximal portion includes a porous coating consisting essentially of first and second layers of metallic spherical particles having average diameters of about 0.022 inches bonded together at their points of contact to define therebetween a plurality of connected interstitial pores.

* * * * *

UNITED STATES PATENT AND TRADEMARK OFFICE
CERTIFICATE OF CORRECTION

PATENT NO. : 5,047,056

DATED : September 10, 1991

INVENTOR(S) : Kenna, Robert V.

It is certified that error appears in the above-identified patent and that said Letters Patent is hereby corrected as shown below:

On the title page, under item "[73] Assignee", after "Pfizer" insert --Hospital Products Group--.

Signed and Sealed this

Sixteenth Day of March, 1993

Attest:

STEPHEN G. KUNIN

Attesting Officer

Acting Commissioner of Patents and Trademarks